United States Patent [19]

McCue et al.

[11] Patent Number: 5,403,587
[45] Date of Patent: Apr. 4, 1995

[54] DISINFECTANT AND SANITIZING COMPOSITIONS BASED ON ESSENTIAL OILS

[75] Inventors: Karen A. McCue, Tenafly; Dennis T. Smialowicz, Waldwick, both of N.J.

[73] Assignee: Eastman Kodak Company, Rochester, N.Y.

[21] Appl. No.: 52,198

[22] Filed: Apr. 22, 1993

[51] Int. Cl.$^6$ .................. A61K 35/78; A61K 31/20
[52] U.S. Cl. .................. 424/195.1; 514/558; 514/937; 514/938; 514/942; 514/943
[58] Field of Search .................. 424/195.1; 514/558, 514/937, 938, 942, 943

[56] References Cited

U.S. PATENT DOCUMENTS

| | | | |
|---|---|---|---|
| 3,688,985 | 9/1972 | Engel | 239/54 |
| 4,251,383 | 2/1981 | Kemp | 252/118 |
| 4,318,906 | 3/1982 | Llopart | 424/195.1 |
| 4,533,487 | 8/1985 | Jones | 252/170 |

Primary Examiner—John W. Rollins
Assistant Examiner—Howard C. Lee
Attorney, Agent, or Firm—J. Jeffrey Hawley

[57] ABSTRACT

The present invention provides an aqueous antimicrobial composition containing one or more essential oils which exhibit antimicrobial properties and which can be combined with a water carrier and a solubilizing or dispersing agent to form a solution or a dispersion of the essential oil in the water carrier, said essential oil exhibiting antimicrobial properties when incorporated in said water carrier.

9 Claims, No Drawings

DISINFECTANT AND SANITIZING COMPOSITIONS BASED ON ESSENTIAL OILS

FIELD OF THE INVENTION

This invention relates to aqueous antimicrobial compositions which can used to sanitize, disinfect and clean hard surfaces. The compositions include essential oils having antimicrobial properties.

BACKGROUND OF THE INVENTION

Antimicrobial compositions include materials which have the ability to sanitize and/or disinfect. It is generally recognized that a sanitizing material greatly reduces the microorganisms existing on a hard surface and that a disinfecting material eliminates the microorganisms existing on a hard surface. However, current antimicrobial compositions, including sanitizers and disinfectants, contain antimicrobial agents which are not naturally occurring. For example, typical antimicrobial agents used in sanitizers and disinfectants include phenolic compounds, quaternary compounds, and halogen containing compounds. Such materials are not natural and are prepared through chemical processing and synthesis.

Antimicrobial ingredients often are difficult to prepare in a form which permits easy incorporation into an aqueous media. Often these antimicrobial ingredients are not easily dispersed in water and can be lumpy materials, wet pastes or viscous liquids. In such forms, active antimicrobial ingredients are often difficult to handle and pose problems when attempts are made to incorporate them into a final aqueous mixture.

Thus, it would be desirable to produce antimicrobial compositions used to treat hard surfaces which are easy to formulate into a homogenous aqueous mixture. Such a form would aid in the application and the efficacy of the resulting antimicrobial composition. Moreover, because of environmental concerns, it would be desirable to use more natural and environmentally acceptable antimicrobial ingredients in consumer products such as sanitizers, disinfectants and disinfectant cleaners.

Both synthetic essential oils and naturally occurring botanical essential oils have been mentioned for fragrant, medicinal, antiseptic and insecticidal uses. For example, U.S. Pat. No. 3,688,985 discloses emulsions of essential oils, such as methyl salicylate, that are impregnated into water insoluble resins. Thymol, a compound found in thyme oil, is also mentioned. The impregnated solid resin is used to disseminate a fragrance or medicinal vapor into a room. This patent also asserts that the resin may be impregnated with a sanitizing material but does not identify any such sanitizing material specifically for use.

Essential oils are volatile oils distilled or extracted from plants. Typical essential oils are those obtained from thyme, lemongrass, citrus, anise, clove, aniseed, roses, lavendar, citronella, eucalyptus, peppermint, camphor, sandalwood, cinnamon leaf and cedar. Essential oils are widely used in perfumery, as food flavorings, medicine and solvents. However, because of their hydrophobic nature, essential oils cannot easily be formulated into aqueous mixtures.

SUMMARY OF THE INVENTION

It has been discovered that certain essential oils which display antimicrobial efficacy are capable of being solubilized or dispersed when combined in appropriate amounts with water and a solubilizing or dispersing agent. These antimicrobial compositions may be used as hard surface sanitizers, disinfectants and disinfectant cleaners.

It is the object of this invention to provide an aqueous antimicrobial composition which can be used on hard surfaces. It is another object of this invention that the antimicrobial efficacy of the compositions contemplated by this invention result from the presence of one or more essential oils. It is the further object of this invention to provide aqueous compositions which can be used as sanitizers, disinfectants and disinfectant cleaners.

Another object of this invention is to provide a method of formulating aqueous antimicrobial compositions in which the antimicrobial agent(s) is one or more essential oils.

A further object of this invention is to provide a method of treating hard surfaces with the compositions contemplated by this invention in order to sanitize, disinfect and clean the hard surface to which the compositions are applied.

These objects as well as others, which will become apparent from the description which follows, are achieved by forming a novel aqueous antimicrobial composition containing one or more essential oils which exhibit antimicrobial properties and which can be combined with a water carrier and a solubilizing or dispersing agent to form a solution or a dispersion of the essential oil in the water carrier, said essential oil exhibiting antimicrobial properties when incorporated in said water carrier.

It should be understood that the foregoing description of the invention is intended to be illustrative and that other embodiments and modifications may be apparent to those skilled in the art without departing from the spirit and scope of the invention. For example the antimicrobial active component of the essential oil may be extracted and used in the compositions of the invention, with appropriate concentration adjustments.

DETAILED DESCRIPTION OF THE INVENTION

The present invention provides novel aqueous antimicrobial compositions which, because of the presence of one or more essential oils which exhibit antimicrobial properties significantly reduce or eliminate harmful microorganisms from hard surfaces to which the compositions are applied. In general, the antimicrobial compositions of this invention comprise an essential oil which is capable of being solubilized or dispersed in a water carrier when mixed in appropriate quantities with said water carrier and one or more solubilizing or dispersing agents, said essential oil exhibiting antimicrobial properties when incorporated in said water carrier.

The resulting essential oil solution or dispersion is a homogenous aqueous mixture which permits easy and effective application of the composition to a hard surface. The compositions of this invention permit the antimicrobial essential oils to evenly coat the hard surface to which the solution or dispersion is applied so that any microorganisms present can be effectively eliminated.

The aqueous antimicrobial compositions of this invention comprise:

a) an antimicrobially effective amount of an essential oil capable of being dissolved or dispersed in a water carrier and exhibiting antimicrobial properties when incorporated in a water carrier;

b) a solubilizing or dispersing amount of a solubilizing or dispersing agent sufficient to form an aqueous solution or dispersion of said essential oil in a water carrier; and c) sufficient water to make 100 weight percent.

In preferred embodiments, the compositions of the present invention comprise:

a) about 0.02 to about 5 weight percent of one or more essential oils capable of imparting antimicrobial properties when incorporated in a water carrier;

b) about 0.10 to about 95 weight percent of a solubilizing or dispersing agent for the essential oil; and c) sufficient water to make 100 weight percent.

Another useful embodiment in which the essential oil is solubilized in the water carrier is an aqueous sanitizing or disinfecting composition wherein said composition comprises:

a) 0.02 to 5.0 weight percent of an essential oil;

b) 2.75 to 30 weight percent of an organic solvent;

c) 0.75 to 10 weight percent of a surfactant; and d) sufficient water to make 100 weight percent, wherein the pH of the composition is between about 2 and 5.

Another useful embodiment is a composition comprising:

a) about 0.2 weight percent of thyme oil or lemongrass oil;

b) about 85 weight percent ethanol;

c) about 0.2 weight percent lauryl dimethyl amine oxide; and d) about 14.6 weight percent water wherein said composition has a pH of about 9.6.

The components of our antimicrobial compositions are combined in such a manner and in such amounts to produce an aqueous mixture wherein said essential oil is dissolved or dispersed in a water carrier and, in which the essential oil demonstrates antimicrobial properties in said water carrier against a variety of microorganisms, bacteria, viruses and fungi and which can be used as a hard surface sanitizer, disinfectant and/or disinfectant cleaner. The antimicrobial compositions of this invention, when properly formulated, results in either a solution or dispersion of the essential oil in a water carrier which is stable, clear and displays antimicrobial effectiveness. These compositions can be used as a hard surface sanitizer, disinfectant and/or disinfectant cleaner.

The essential oils contemplated for use in the aqueous compositions of this invention are those essential oils which exhibit antimicrobial activity and which can form a solution or dispersion when combined with a water carrier and a solubilizing or dispersing agent wherein said essential oil exhibits antimicrobial activity in said water carrier. Such essential oils include, but are not limited to, those obtained from thyme, lemongrass, lemons, oranges, anise, clove, roses, lavendar, citronella, eucalyptus, peppermint, camphor, sandalwood and cedar and combinations thereof. Preferred essential oils include thyme oil, lemongrass oil, lemon oil, anise oil, orange oil and clove oil. The most preferred essential oils are thyme oil and lemongrass oil. While essential oils which display antimicrobial efficacy are preferred, the compositions of this invention also contemplate the use of chemical compounds or active antimicrobial agents which have antimicrobial efficacy contained in said essential oils.

The solubilizing and dispersing agents employed should be capable, when mixed with water and an essential oil exhibiting antimicrobial efficacy, of forming a solution or dispersion. Preferably, the solubilizing agent will be used to form a homogeneous aqueous solution when combined with water and the essential oils of this invention. Preferred solubilizing and dispersing agents include solvents and surfactants.

The organic solvents contemplated for use as solubilizing or dispersing agents include various alcohols containing 1 to 6 carbon atoms, glycols and glycol ethers. Preferred solvents include methanol, ethanol, ispropanol, propylene glycol and hexylene glycol. The most preferred solvents are ethanol, isopropanol and propylene glycol.

Surfactants, while capable of solubilizing or dispersing essential oils contemplated by this invention, because of their ability to act as a cleaner or detergent, are present in the preferred compositions of this invention. The surfactants contemplated for use in the antimicrobial compositions of this invention can be anionic or amphoteric. Representative surfactants which can be used include a combination of a nonoxynol-10 carboxylic acid, alkyl aryl sulfonates, lauryl sulfates, linear alkylbenezene sulfonate isopropylamine salt (Ninate 411), sodium laureth sulfate (Witcolate TM ES3N), hydroxyethyl olcylimidazoline (Unamine® O), ethyoxylated fatty alcohol carboxylate free acid form (Surfine WNT-A), triethanolamine, dodecylbenzene sulfonate (Calsoft T-60), secondary alkane sulfonate, sodium salt (Hostapur SAS 60), coco fatty acid-sodium salt (Norfox Coco powder), sodium cumene sulfonate, sodium xylene sulfonate and other sulfonates such as amino alkylaryl sulfonate, and sulfonates from fatty acids. Preferred surfactants include dodecylbenzene sulfonate, lauryl dimethyl amine oxide, ethoxylated fatty alcohol carboxylate free acid form, and sodium lauryl sulfate (Standapol WAQ-LC). The most preferred surfactants are dodecylbenzene sulfonate, lauryl dimethyl amine oxide and sodium lauryl sulfate.

Water is included as carrier in an amount sufficient to make the total composition 100 weight percent. The pH of the compositions contemplated by this invention can range from 1 to about 12 but is dependent upon the quantity and type solubilizing agent used and essential oil. For example, with thyme oil and ethanol as the solvent the preferred pH is lower with lower solvent levels. The preferred pH range of the antimicrobial compositions of this invention is about 2–6.

One or more other ingredients may optionally be included in the compositions of the invention in order to provide aesthetic or other beneficial properties thereto. Such optional ingredients are, for example, additional antimicrobial agents, deodorizers, coloring agents, fragrances, emulsifiers, solubilizers, corrosion inhibitors and solvents. The only requirement being that for any particular composition such optional ingredients be compatible with the other ingredients present herein.

By way of example, optional ingredients which may be incorporated include the following:

Antimicrobials: phenolic compounds such as o-penylphenol, o-benzyl[p-chlorophenol] and 4-tertamylphenol; quaternary ammonium compounds such as alkyl dimethyl benzyl ammonium chloride, octyl decyl dimethyl ammonium chloride, dioctyl dimethyl ammonium chloride, didecyl dimethyl ammonium chloride and alkyl dimethyl benzyl ammonium saccharinate.

Deodorizer: N-alkyl-N-ethylmorpholinium ethyl sulfate.

Emulsifiers/Solubilizers: lauryl dimethyl amine oxide, polyoxypropylene, polyoxyethylene block copolymers and anionic, cationic and nonionic surfactants.

Corrosion Inhibitors: mono- and triethanolamine, ammonium hydroxide, sodium molybdate, sodium benzoate and tetra sodium ethylenediamine tetraacetate.

Other optional ingredients, as well as the amounts of the optional ingredients which can be employed, can readily be determined by one skilled in the art. For example, the phenolic and quaternary ammonium antimicrobial agents generally will not exceed a concentration of about 0.2 percent by weight in the final aqueous composition.

The compositions of the invention may be formulated with conventional propellants for dispensing as aerosols from conventional pressurized containers. Propellants which may be used are well known and conventional in the art and include, for example, isobutane, n-butane, propane, dimethyl ether and blends thereof as well as individual or mixtures of chlorofluoro- and/or fluorohydrocarbons. The amount of propellant employed should provide a suitable spray pattern and for essentially complete expulsion of the composition from the aerosol container. The appropriate amount to be used for any particular aerosol propellant system can readily be determined by one skilled in the art. Generally speaking, the amount of a particular propellant employed should provide an internal pressure of from about 30 to about 100 p.s.i.g.

The compositions of this invention can be prepared by entirely conventional procedures known to those of ordinary skill in the art. For example, the compositions can be formulated by preparing an aqueous mixture of the solubilizing agent and essential oils. The resulting mixture can then be agitated until a dispersion or solution is formed.

The compositions can be packaged in conventional, ready-to-use dispensing systems. Thus they can be packaged in aerosol form in conventional aerosol containers or in liquid form in trigger pump spray bottles and squeeze bottles or pump spray bottles to produce an aerosol using a pump mechanism to build the necessary pressure to produce the aerosol. The compositions can also be impregnated into towelettes which can then be placed into contact with the hard surface to be treated. These towelettes can be packaged individually or in bulk form for individual dispensing.

The compositions of this invention have been found useful for reducing or eliminating the bacteria and other harmful microorganisms on a variety of surfaces contaminated with said bacteria and other harmful microorganisms. Application of the compositions contemplated by this invention to hard surface significantly reduces the potential of disease associated with the microorganisms through contact with contaminated surfaces. The compositions of this invention are contacted with the surface to be treated in any of a variety of methods conventional sanitizers, disinfectants or cleaners are applied to a hard surface (e.g. spray, immersion, wipe, etc.). The composition is then permitted to remain in contact with the surface being treated for a period of time sufficient to reduce or eliminate the microorganisms existing on the treated surface. The time required for effective treatment of a given hard surface is dependent upon a variety of factors including, but not limited to, the particular antimicrobial composition applied, type and quantity of microorganisms present and ambient conditions. While not required, the surface can then be rinsed or wiped clean to remove the composition.

The compositions contemplated by this invention can be used to sanitize, disinfect and/or clean, depending upon the formulation used, any hard surface onto which the aqueous composition is applied. Hard surfaces which can be treated with the compositions of this invention include countertops, tiles, porcelain products such as sinks and toilets, floors, windows, eating utinsils, glassware, dishes, dental and surgical instruments.

The compositions of the invention are illustrated by examples of specific formulations described below without, however, being limited thereto.

BRIEF DESCRIPTION OF TEST METHODS

Methods I and II

Formulations were tested for antimicrobial effectiveness against *Staphylococcus aureus* (ATCC 6538) by the AOAC Use Dilution (Method I) and Germicidal Spray Test (Method II) as outlined in the Official Methods of Analysis of the Association of Official Analytical Chemists 15 ed. 1990. These tests are used to evaluate microbiological activity for practical disinfection on hard surface carriers.

The AOAC USE Dilution Test is used to evaluate liquid-type products while the AOAC Germicidal Spray Test is used to evaluate spray-type products. In both tests, a hard surface is contaminated with test microorganisms with a broth culture. After the hard surface or carrier is dried, it is immersed or sprayed for ten minutes with the individual composition to be evaluated. The carrier is then subcultured into nutrient medium containing a neutralizer. The carrier in the nutrient medium is incubated for 48 hours. After 48 hours, the carriers are observed for growth of survivors.

Ten to sixty carriers are examined for bacterial growth after contact with the test formulations. Test results are expressed in terms of the number of positive carriers; i.e. carriers with growth of the test organism, out of the number of carriers tested. Antimicrobial effectiveness is observed with those formulations showing no more than 1+ (growth) carrier.

Microbial Reduction Assay

Formulations were tested for antimicrobial activity by a Microbial Reduction Assay. Ten mls. of the test formulation is inoculated with a bacterial suspension and mixed. The suspension remains in contact with the test formulation for 5 minutes. After this time, aliquots are withdrawn and plate counts conducted for enumeration of survivors and calculation of percent reduction. Antimicrobial effectiveness is observed with those formulations showing a 99.9% (3 log) reduction of bacteria.

EXAMPLES

Example 1

Four different compositions, two within the scope of the invention, were prepared to illustrate the present invention. The compositions are presented in Table I below. Compositions A and B are comparative compositions not within the scope of the invention. (Each composition in all of the compositions below contained water to 100 weight percent.)

The data shows that compositions 1 and 2 both containing a combination of thyme oil, ethanol and water show disinfectant activity. In addition composition 2 has the added advantage in that the thyme oil dissolves in the composition in the presence of a surfactant.

The following is a description of the preparation of Composition 2.

A solution of ethanol and water was prepared. To this solution, thyme oil was added and agitated until a homogeneous mixture was formed. While the homogeneous mixture was still being agitated, dodecyl benzene sulfonate (Calsoft T-60) and ethoxylated fatty alcohol carboxylate-free acid form (Surfine WNT-A) were added. The resulting composition had a pH of about 2.9.

one positive carrier out of 60 tested. A disinfectant product, when properly formulated is soluble, stable, clear and effective. Formulation 2 with an essential oil thyme, solvent, and surfactants in an aqueous carrier demonstrates disinfectant activity against *S. aureus* showing no more than one positive out of 60 carriers tested.

Example 2

Other essential oils used in compositions within the scope of this invention were tested. Concentrations are given in weight percent. The compositions were made in a manner similar to Composition 2 of Example 1. The results are presented in Table II. The data therein show that all of the compositions with the listed essential oils exhibit antimicrobial activity by passing the tests used in example for evaluation.

TABLE II

| | | | Microbiological Results AOAC USE DILUTION TEST | | | | | |
|---|---|---|---|---|---|---|---|---|
| | Essential Oil & Conc. | Ethyl alcohol | Surfactant | | pH | *S. aureus* #Carriers +/#Tested | Activity | Water Solubility |
| | | | Surfine WNT-A | Calsoft T-60 | | | | |
| 3 | Lemongrass 0.25 | 15.0 | 1.5 | 0.25 | 2.8 | 0/10 | Pass | Soluble |
| 4 | Lemon 0.1 | 15.0 | 1.5 | 0.25 | 3.0 | 1/10 | Pass | Soluble |
| 5 | Orange 0.1 | 15.0 | 1.5 | 0.25 | 3.0 | 0/10 | Pass | Soluble |
| 6 | Anise 0.1 | 15.0 | 1.5 | 0.25 | 3.0 | 0/10 | Pass | Soluble |
| 7 | Clove 0.1 | 15.0 | 1.5 | 0.25 | 3.0 | 0/10 | Pass | Soluble |

TABLE I

| | | | Microbiological Results AOAC USE DILUTION TEST | | | | | |
|---|---|---|---|---|---|---|---|---|
| | Thyme Oil | Ethyl alchohol | Surfactant | | pH | *S. aureus* #Carriers + (growth)/ #tested | Activity | Solubility in water |
| | | | Surfine WNT-A | Calsoft T-60 | | | | |
| A | 0.15 | — | — | — | 3.0 | 4+/60 | Fail | Not Soluble |
| B | — | 15.0 | — | — | 3.0 | 60+/60 | Fail | Soluble |
| 1 | 0.15 | 15.0 | — | — | 3.1 | 1+/60 | Pass | Not Soluble |
| 2 | 0.15 | 15.0 | 1.5 | 0.25 | 2.9 | 1+/60 | Pass | Soluble |

In Table I neither thyme oil (Composition A) nor ethanol alone (Composition B) has disinfectant activity. In Formulation A, thyme was not soluble in water alone and the test with the composition exhibited 4 positives (with growth) out of 60 carriers tested. In Formulation B, the alcohol in water was soluble but against *S. aureus* showed 60 carriers with growth (60+) out of 60 tested.

When essential oil thyme was added to the solvent ethanol in (Formulation 1), the formulation was effective against *S. aureus* organism showing no more than

Example 3

The following screening data set out in Table III establishes the range of effective disinfectant concentrations of essential oils and solvent in the compositions of this invention. In the table, compositions 15-C have a pH of 9.6. Compositions 15-16 containing both thyme oil and a high content of ethanol is an effective disinfectant at the high pH. Composition C, a comparitive example without thyme oil, was ineffective. Compositions 8-14 had a pH of 2.95 to 3.32.

TABLE III

| | | | Microbiological Results DATA TO SUBSTANTIATE RANGE | | | | | |
|---|---|---|---|---|---|---|---|---|
| | | | | | | *S. aureus* | | |
| | Thyme Oil Concentration | Ethyl alcohol | Surfactant | | pH | AOAC Use Dilution #Carriers | AOAC Germicidal Spray +/#tested | Activity |
| | | | Surfine WNT-A | Calsoft T-60 | | | | |
| 8 | 0.02 | 2.75 | 1.5 | 0.25 | 2.95 | 1/10 | | pass |
| 9 | 0.02 | 30.00 | 1.5 | 0.25 | 3.07 | 1/10 | | pass |
| 10 | 5.00 | 2.75 | 1.5 | 0.25 | 3.32 | 0/10 | | pass |
| 11 | 5.00 | 30.00 | 1.5 | 0.25 | 3.15 | 0/10 | | pass |
| 12 | 0.15 | 1.0 | — | — | 3.07 | 0/10 | | pass |
| 13 | 0.15 | 4.8 | — | — | 3.2 | 0/10 | | pass |
| 14 | 0.15 | 0.10 | — | — | 3.2 | 0/10 | | pass |
| 15 | 0.025 | 85.0 | LAURYL | | 9.6 | | 0/30 | pass |

TABLE III-continued

Microbiological Results
DATA TO SUBSTANTIATE RANGE

|  | Thyme Oil Concentration | Ethyl alcohol | Surfactant | | pH | S. aureus | | Activity |
|---|---|---|---|---|---|---|---|---|
|  |  |  | Surfine WNT-A | Calsoft T-60 |  | AOAC Use Dilution #Carriers | AOAC Germicidal Spray +/#tested |  |
| 16 | 0.20 | 85.0 | DIMETHYL AMINE OXIDE 0.2 LAURYL DIMETHYL AMINE OXIDE 0.2 | | 9.6 |  | 1/60 | pass |
| C |  | 85 | LAURYL DIMETHYL AMINE OXIDE 0.2 | | 9.6 |  | 5/60 | fail |

Example 4

Another antimicrobial composition (Composition 17) according to the invention was prepared following the process described in Example 1. This composition was used and tested in accordance with the Microbiocidal Reduction Assay described previously.

The composition of this example was compared with a mixture which did not contain an essential oil (Composition D). The composition of the invention passed the test while the comparative composition did not.

TABLE IV

Microbiological Results
MICROBIAL REDUCTION ASSAY

|  | Thyme Oil | Ethyl Alcohol | Surfactant Standapol WAQ-LC | pH | Percent Reduction 5 Minute Contact | | Activity |
|---|---|---|---|---|---|---|---|
|  |  |  |  |  | S. aureus | P. aeruginosa |  |
| 17 | 0.25 | 15.0 | 6.6 | 8.9 | 99.99 | 99.99 | pass |
| D | — | 15.0 | 6.6 | 9.0 | 93.0 | 50.00 | fail |

Example 5

Additional antimicrobial compositions according to the invention were prepared following the process described in Example 1. The results are shown in Table V. This example again illustrates the value of essential oils for germicidal activity. Compositions E and F, without botanical oils, are not effective against S. aureus showing 5 carriers with growth. Compositions 18, 19, 20 and 21, with essential oils and having a pH of 5 and 9.6 exhibit disinfectant activity against S. aureus showing no more than 1 carrier with growth.

can be effected within the spirit and scope of the invention.

We claim:

1. An aqueous antimicrobial composition comprising:
   a) 0.02 to 5.0 weight percent of an essential oil capable of being dissolved or dispersed in a water carrier and exhibiting antimicrobial properties when incorporated in a water carrier;
   b) a solubilizing or dispersing agent sufficient to form an aqueous solution or dispersion of said essential oil in a water carrier said solubilizing or dispersing agent comprising from 2.75 to 30 weight percent of said composition of an organic solvent and from 0.75 to 10 weight percent of said composition of a surfactant; and
   c) sufficient water to make 100 weight percent.

2. An aqueous antimicrobial composition according to claim 1, wherein said composition comprises:
   a) about 0.02 to about 5 weight percent of said essential oil;
   b) about 0.10 to about 85 weight percent of said solubilizing or dispersing agent for the essential oil; and
   c) sufficient water to make 100 weight percent.

TABLE V

Microbiological Results
AOAC GERMICIDAL SPRAY TEST

|  | ESSENTIAL OIL/ CONCENTRATION | ETHYL ALCOHOL | SURFACTANT | | pH | #+CARRIERS/#TESTED | | Activity |
|---|---|---|---|---|---|---|---|---|
|  |  |  | SURFINE WNT-A | CALSOFT T-60 |  | S. aureus | S. choleraesuis |  |
| 18 | THYME OIL 0.15 | 15.0 | 1.5 | 0.25 | 5.0 | 0/10 | 0/10 | pass |
| 19 | LEMON-GRASS OIL 0.15 | 15.0 | 1.5 | 0.25 | 5.0 | 0/10 | 0/10 | pass |
| E | — | 15.0 | 1.5 | 0.25 | 5.0 | 5/10 | 4/10 | fail |
| 20 | THYME OIL 0.20 | 85.0 | LAURYL DIMETHYL AMINE OXIDE 0.2% | | 9.6 | 1/60 |  | pass |
| 21 | LEMON-GRASS OIL 0.20 | 85.0 | LAURYL DIMETHYL AMINE OXIDE 0.2% | | 9.6 | 0/60 |  | pass |
| F | — | 85.0 | LAURYL DIMETHYL AMINE OXIDE 0.2% | | 9.6 | 5/60 |  | fails |

The invention has been described in detail with particular reference to preferred embodiments thereof, but it will be understood that variations and modifications 3. The composition of claim 1 wherein the essential oil is selected from the group consisting of lemongrass, lemon, orange, anise, clove, thyme and mixtures of each.

4. The composition of claim 3 wherein the essential oil is lemongrass oil, thyme oil and mixtures of each.

5. The composition of claim 4 wherein the pH is 2.9 to 3.2.

6. An aqueous antimicrobial composition according to claim 4 having a pH of 1 to 12 and wherein said solubilizing or dispersing agent comprises ethanol and lauryl dimethylamine oxide, said composition comprising 0.02–0.25 weight percent of said essential oil; 15.00 to 85 weight percent of ethanol, 0.1 to 10 weight percent of lauryl dimethylamine oxide and sufficient water to make a total of 100 weight percent.

7. The composition of claim 1 wherein said organic solvent is selected from the group consisting of ethyl alcohol, hexylene glycol, propylene glycol and diethylene glycol n-butyl ether and mixtures of each.

8. The composition of claim 1 wherein the surfactant is selected from the group consisting of linear alkylbenzene sulfonate isopropylamine salt, sodium laureth sulfate, hydroxyethyl olcylimidazoline, ethoxylated fatty alcohol carboxylate, free acid form, nonoxynol-10 carboxylic acid, triethanolamine dodecylbenzene sulfonate, secondary alkane sulfonate, sodium salt, coco fatty acid sodium salt, Na cumene sulfonate, Na xylene sulfonate, and sodium lauryl sulfate.

9. An antimicrobial composition according to claim 1 wherein said solubilizing or dispersing agent comprises ethanol and lauryl dimethyl amine oxide, said composition comprising:
a) about 0.2 weight percent of thyme oil or lemongrass oil;
b) about 85 weight percent ethanol;
c) about 0.2 weight percent lauryl dimethyl amine oxide; and
d) about 14.6 weight percent water wherein said composition has a pH of about 9.6.

* * * * *